(12) United States Patent
Lowe et al.

(10) Patent No.: US 6,841,157 B2
(45) Date of Patent: Jan. 11, 2005

(54) PRODUCTION OF CHIMERIC HUMAN PAPILLOMAVIRUS

(75) Inventors: Robert S. Lowe, Harleysville, PA (US); Craig M. Meyers, Hummelstown, PA (US); Jiaping Zhang, Cranbury, NJ (US); Michelle Kaupas, Plymouth Meeting, PA (US); Kathrin Ute Jansen, Doylestown, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/332,553

(22) PCT Filed: Jul. 3, 2001

(86) PCT No.: PCT/US01/21201
§ 371 (c)(1),
(2), (4) Date: Jul. 28, 2003

(87) PCT Pub. No.: WO02/04595
PCT Pub. Date: Jan. 17, 2002

(65) Prior Publication Data
US 2004/0043471 A1 Mar. 4, 2004

Related U.S. Application Data

(60) Provisional application No. 60/216,556, filed on Jul. 7, 2002.

(51) Int. Cl.[7] ............................................. A61K 39/12
(52) U.S. Cl. ............................... 424/204.1; 424/205.1; 424/184.1; 435/69.1
(58) Field of Search .......................... 424/204.1, 205.1, 424/184.1; 435/235.1, 6, 236, 69.1; 536/23.74

(56) References Cited

U.S. PATENT DOCUMENTS

| | | | |
|---|---|---|---|
| 5,376,542 A | 12/1994 | Schlegal et al. | |
| 5,576,206 A | 11/1996 | Schlegel et al. | |
| 5,618,536 A | 4/1997 | Lowy et al. | |
| 5,855,891 A | 1/1999 | Lowy et al. | |
| 5,955,087 A | 9/1999 | Whittle et al. | |
| 5,994,115 A | 11/1999 | Meyers et al. | |
| 6,004,557 A | 12/1999 | Edwards et al. | |
| 6,352,696 B1 * | 3/2002 | Hallek et al. ............ | 424/204.1 |

FOREIGN PATENT DOCUMENTS

| | | | |
|---|---|---|---|
| WO | WO 96/19496 | | 6/1996 |
| WO | WO 98/02548 | * | 1/1998 |
| WO | WO 99/04811 | * | 2/1999 |
| WO | WO 02/08264 | * | 1/2002 |

OTHER PUBLICATIONS

Meyers, et al. 1997, J. Virol. 71(10): 7381–86.
Meyers, et al. 1992, Science 257: 971–73.
Kreider et al. 1987, J. Virol 61:590.

* cited by examiner

Primary Examiner—Ali R. Salimi
(74) Attorney, Agent, or Firm—Alysia A. Finnegan; Joanne M. Giesser

(57) ABSTRACT

This invention relates to infectious chimeric papillomaviruses, and especially those where the early genes are from human papillomavirus (HPV) 18, and the late genes are from another HPV. Also presented are methods of culturing the virus in raft cell cultures, and to assays utilizing these chimeric viruses.

9 Claims, 8 Drawing Sheets

GENERATE CHIMERIC PLASMID CONTAINING EARLY GENES FROM HPV TYPE 18 AND
L2 AND L1 STRUCTURAL GENES FROM A NON-HPV TYPE 18 SOURCE

↓

INTRODUCE CHIMERIC PLASMID INTO CELLS

↓

GROW CELLS IN RAFT CULTURE TO SUPPORT VIRUS REPLICATION

↓

IDENTIFY CELLS CONTAINING CHIMERIC VIRUS BY
DNA, RNA, AND PROTEIN ANALYSIS

↓

ISOLATE VIRUS AND DEMONSTRATE INFECTIVITY IN CULTURED CELLS

FIG.1

SEQUENCE LISTING

```
<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: PCR probe

<400> SEQUENCE: 1
cggccagacg tcggctgcta cacg                                              24

<210> SEQ ID NO 2
<211> LENGTH: 38
<212> TYPE: DNA
<213> ORGANISM: Artificial Sequence
<220> FEATURE:
<223> OTHER INFORMATION: PCR probe

<400> SEQUENCE: 2
```

-continued gctagcagat ctacttttat tacaaaaata caaaaagc            38

<210> SEQ ID NO 3
<211> LENGTH: 29
<212> TYPE: DNA
<213> ORGANISM: Artificial Sequence
<220> FEATURE:
<223> OTHER INFORMATION: PCR probe

<400> SEQUENCE: 3
gtatgcaatt agcttaagta aaacaaac                       29

<210> SEQ ID NO 4
<211> LENGTH: 40
<212> TYPE: DNA
<213> ORGANISM: Artificial Sequence
<220> FEATURE:
<223> OTHER INFORMATION: PCR probe

<400> SEQUENCE: 4
gctagcagat cttatgtgtg tgtgtatata tatatacatc          40

<210> SEQ ID NO 5
<211> LENGTH: 38
<212> TYPE: DNA
<213> ORGANISM: Artificial Sequence
<220> FEATURE:
<223> OTHER INFORMATION: PCR probe

<400> SEQUENCE: 5
gctagcagat ctatgcgaca caaacgttct gcaaaacg            38

<210> SEQ ID NO 6
<211> LENGTH: 41
<212> TYPE: DNA
<213> ORGANISM: Artificial Sequence
<220> FEATURE:
<223> OTHER INFORMATION: PCR probe

<400> SEQUENCE: 6
gctagcagat ctttacagct tacgttttt gcgtttagca g         41

<210> SEQ ID NO 7
<211> LENGTH: 35
<212> TYPE: DNA
<213> ORGANISM: Artificial Sequence
<220> FEATURE:
<223> OTHER INFORMATION: PCR probe

<400> SEQUENCE: 7
catacataca ttctatgaac tccactattt tggag               35

<210> SEQ ID NO 8
<211> LENGTH: 35
<212> TYPE: DNA
<213> ORGANISM: Artificial Sequence
<220> FEATURE:
<223> OTHER INFORMATION: PCR probe

<400> SEQUENCE: 8
ctccaaaata gtggagttca tagaatgtat gtatg               35

<210> SEQ ID NO 9
<211> LENGTH: 23
<212> TYPE: DNA
<213> ORGANISM: Artificial Sequence

```
<220> FEATURE:
<223> OTHER INFORMATION: PCR probe

<400> SEQUENCE: 9
caaccgagca cgacaggaac gac                                              23

<210> SEQ ID NO 10
<211> LENGTH: 22
<212> TYPE: DNA
<213> ORGANISM: Artificial Sequence
<220> FEATURE:
<223> OTHER INFORMATION: PCR probe

<400> SEQUENCE: 10
caggtccaca atgctgcttc tc                                               22

<210> SEQ ID NO 11
<211> LENGTH: 21
<212> TYPE: DNA
<213> ORGANISM: Artificial Sequence
<220> FEATURE:
<223> OTHER INFORMATION: PCR probe

<400> SEQUENCE: 11
tccaacgacg cagagaaaca c                                                21

<210> SEQ ID NO 12
<211> LENGTH: 20
<212> TYPE: DNA
<213> ORGANISM: Artificial Sequence
<220> FEATURE:
<223> OTHER INFORMATION: PCR probe

<400> SEQUENCE: 12
gagtccacag tgtccaggtc                                                  20

<210> SEQ ID NO 13
<211> LENGTH: 400
<212> TYPE: DNA
<213> ORGANISM: Artificial Sequence
<220> FEATURE:
<223> OTHER INFORMATION: PCR probe

<400> SEQUENCE: 13
caaccgagca cgacaggaac gactccaacg acgcagagaa acacaagtat aatattaagt       60
atgcatggac ctaaggcaac attgcaagac attgtattgc atttagagcc ccaaaatgaa      120
attccggttg accttctatg tcacgagcaa ttaagcgact cagaggaaga aaacgatgaa      180
atagatggag ttaatcatca acatttacca gcccgacgag ccgaaccaca acgtcacaca      240
atgttgtgta tgtgttgtaa gtgtgaagcc agaattgagc tagtagtaga aagctcagca      300
gacgaccttc gagcattcca gcagctgttt ctgaacaccc tgtcctttgt gtgtccgtgg      360
tgtgcatccc agcagtaagc aacaatggct gatccagaag                            400

<210> SEQ ID NO 14
<211> LENGTH: 170
<212> TYPE: DNA
<213> ORGANISM: Artificial Sequence
<220> FEATURE:
<223> OTHER INFORMATION: PCR probe

<400> SEQUENCE: 14
taccagtgac gacacggtat ccgctactca gcttgttaaa cagctacagc acaccccctc       60
```

-continued

```
accgtattcc agcaccgtgt ccgtgggcac cgcaaagacc tacggccaga cgtcggctgc      120
tacacgacct ggacactgtg gactcgcgga gaagcagcat tgtggacctg               170
```

PRODUCTION OF CHIMERIC HUMAN PAPILLOMAVIRUS

This application claims the benefit of Provisional application Ser. No. 60/216,556, filed Jul. 7, 2000.

FIELD OF THE INVENTION

The present invention is directed to infectious chimeric human papillomaviruses (HPVs), and methods for their production. It also includes various assays which utilize these viruses.

BACKGROUND OF THE INVENTION

The ability to generate infectious human papillomaviruses has been hampered by the difficulty in propagating virus in vivo or in vitro. Several methods have been utilized to propagate a few virus types, but these are not useful for all viruses due to the specific replication requirements of each type.
Raft cultures have been used to generate infectious HPV 18 (U.S. Pat. No. 5,994,115 (Meyers); and Meyers et al, 1997 J. Virol. 71(10):7381–6); and HPV 31b (Meyers, et al 1992 Science 257: 971–973 1992). Generation of infectious HPV 11 has also been accomplished using the xenograph mouse model Kreider, et al 1987 J. Virol. 61:590).

The types of infectious HPV generated to date represents only a small number of the over 80 HPV types that have been identified. It would be most desirable to develop a system whereby other HPV serotypes can be conveniently cultured, including chimeric HPVs. Further it would be desirable to develop a sensitive assay which can be used for detecting the presence of infectivity and neutralizing antibodies.

DETAILED DESCRIPTION OF THE INVENTION

This invention relates to infectious chimeric papillomaviruses. In a preferred embodiment, the papillomaviruses are chimeras wherein the early genes (for example, E1, E2, E3, E4, E5, E6 and E7) are from a first papillomavirus and the late genes (L1 and L2) are from a second papillomavirus type. In a preferred embodiment, the early genes are from a human papillomavirus(HPV), and in more preferred embodiments, they are from HPV 18. The late genes, in preferred embodiments, may include other human papillomavirus serotypes or even non-human papillomaviruses (i.e. bovine papillomavirus BPV, cottontail rabbit papillomavirus CRPV, and canine oral papillomavirus COPV.

In embodiments where the late genes are of human papillomavirus origin, they are preferably selected from the group consisting of serotypes which are associates with human diseases, such as genital cancers and warts, i.e. HPV 6a, HPV 6b, HPV 11, HPV 16 and HPV 18. Other serotypes which are preferred include: HPV 1, HPV 31, HPV 33, HPV 35, HPV 39, HPV 41, HPV 47, HPV 51, HPV 57, and HPV 58.

Another aspect of this invention is a method of obtaining infectious chimeric papillomavirus comprising:

a) preparing a chimeric papillomavirus wherein early genes are from a first type of papillomavirus and the late genes are from a second papillomavirus b) preparing a raft cell culture of differentiating epithelial cells;

c) infecting the cell culture with the chimeric papillomavirus, and d) incubating the cell culture under conditions which support viral replication.

Yet another aspect of this invention is an assay to detect the presence of human papillomavirus neutralizing antibody in a serum comprising:

a) contacting a cell culture comprising infectious chimeric papillomavirus with the serum; and b) determining if chimeric papillomavirus replication occurs within the cell culture in the presence of the serum.

In preferred embodiments, this detection is done by contacting the RNA from cells infected with the chimeric virus with reverse transcriptase in order to obtain a cDNA. The cDNA is then amplified in a PCR assay. Optionally the amount of amplified DNA is compared to a control group, such as an otherwise identically infected cell line not exposed to serum.

Yet another aspect of this invention are vectors used to construct the chimeric viruses, and to host cells containing the infectious chimeric papillomaviruses.

BRIEF DESCRIPTION OF THE DRAWINGS

FIG. 1: schematic of the method for making a chimeric HPV

FIG. 2A shows a plasmid containing the genomic sequence of HPV 18 with the coding sequence for the structural proteins L1 and L2 replaced by a Bgl II cloning site. FIG. 2B shows generation of a plasmid containing the genomic sequence of HPV 18 with the coding sequence for the structural proteins L1 and L2 replaced by the homologous proteins of HPV 16.

Figure 2A:
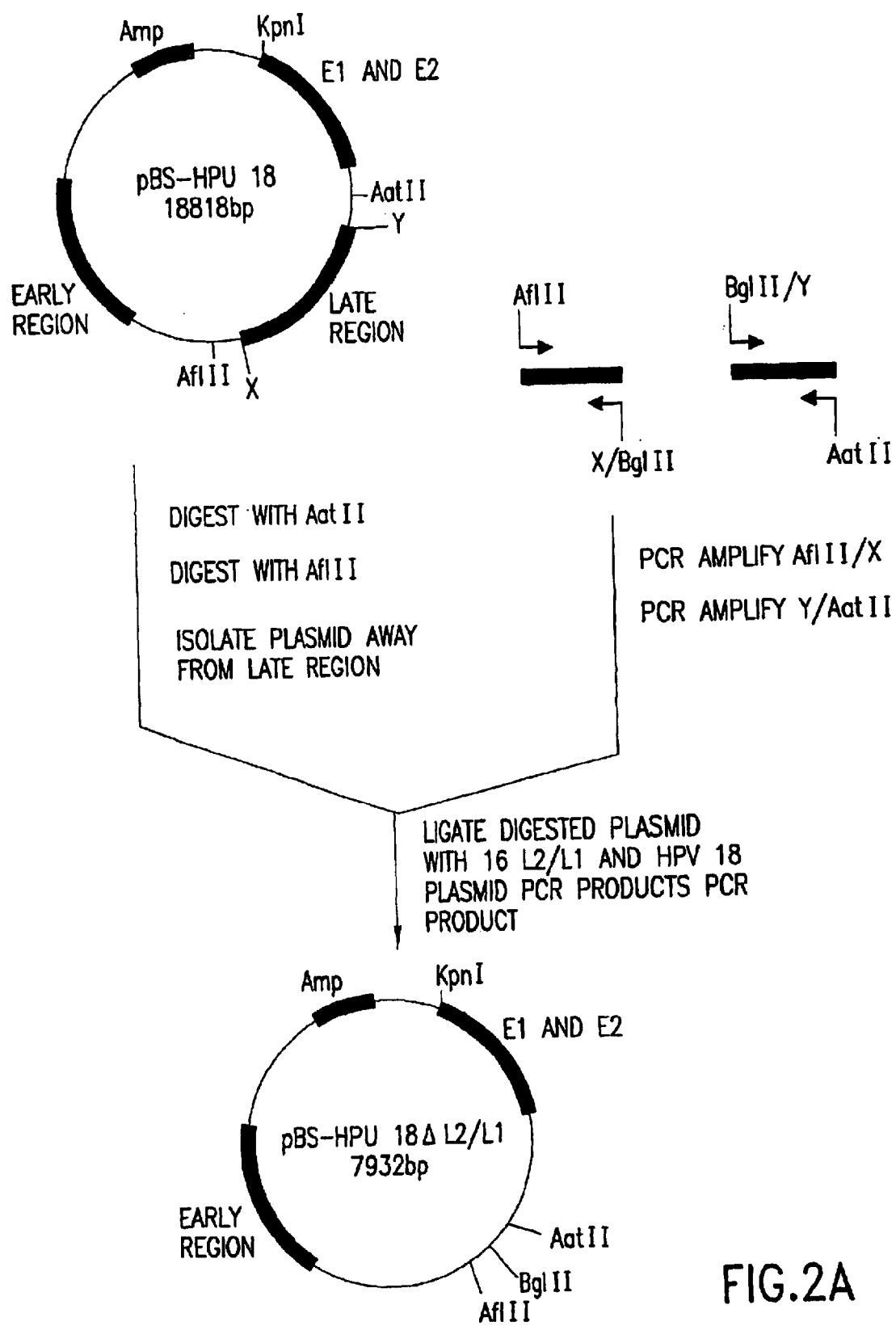
FIGS. 2A and 2B show generation of plasmids with chimeric sequences.
Figure 2B:
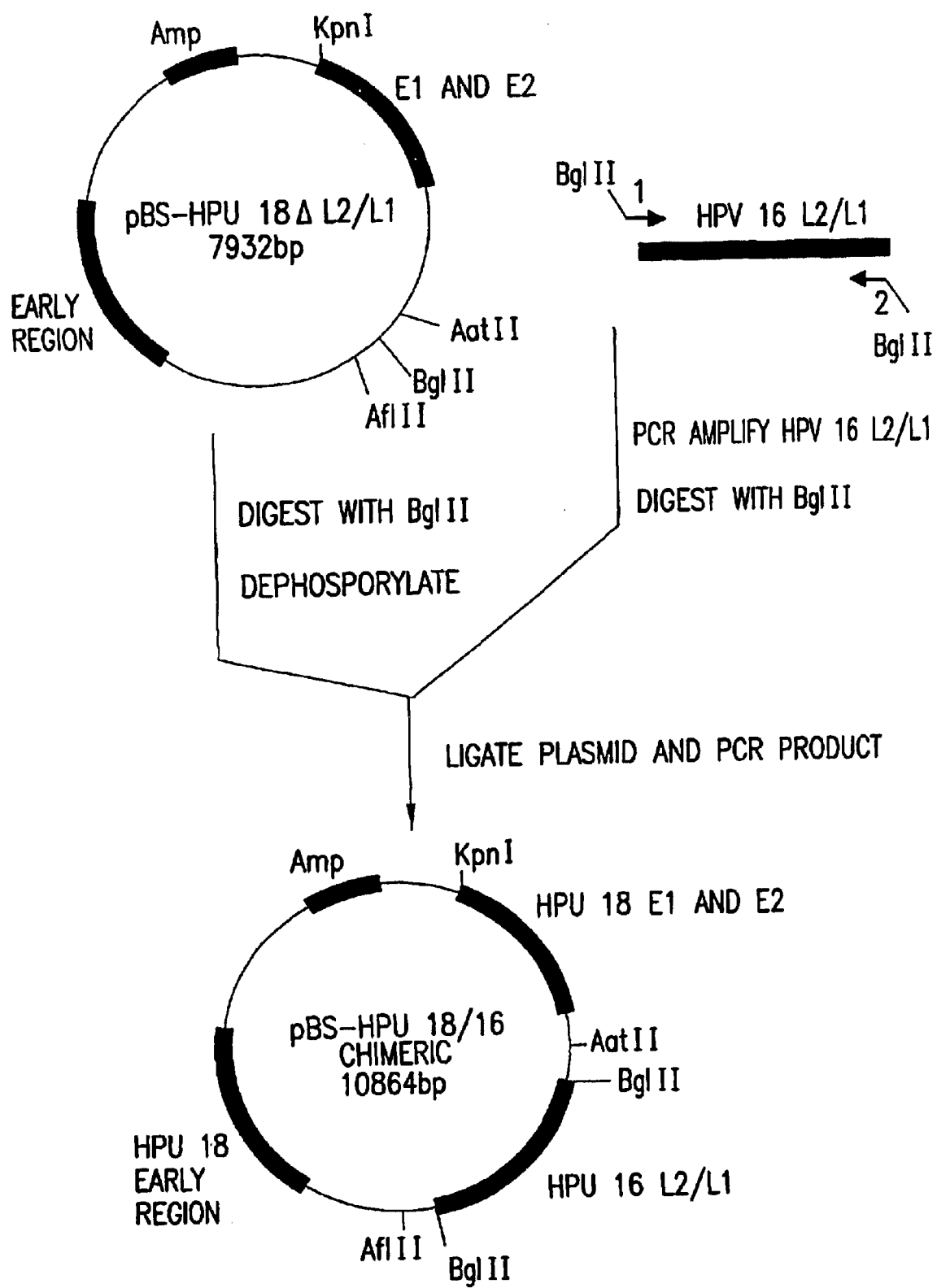
Figure 3A:
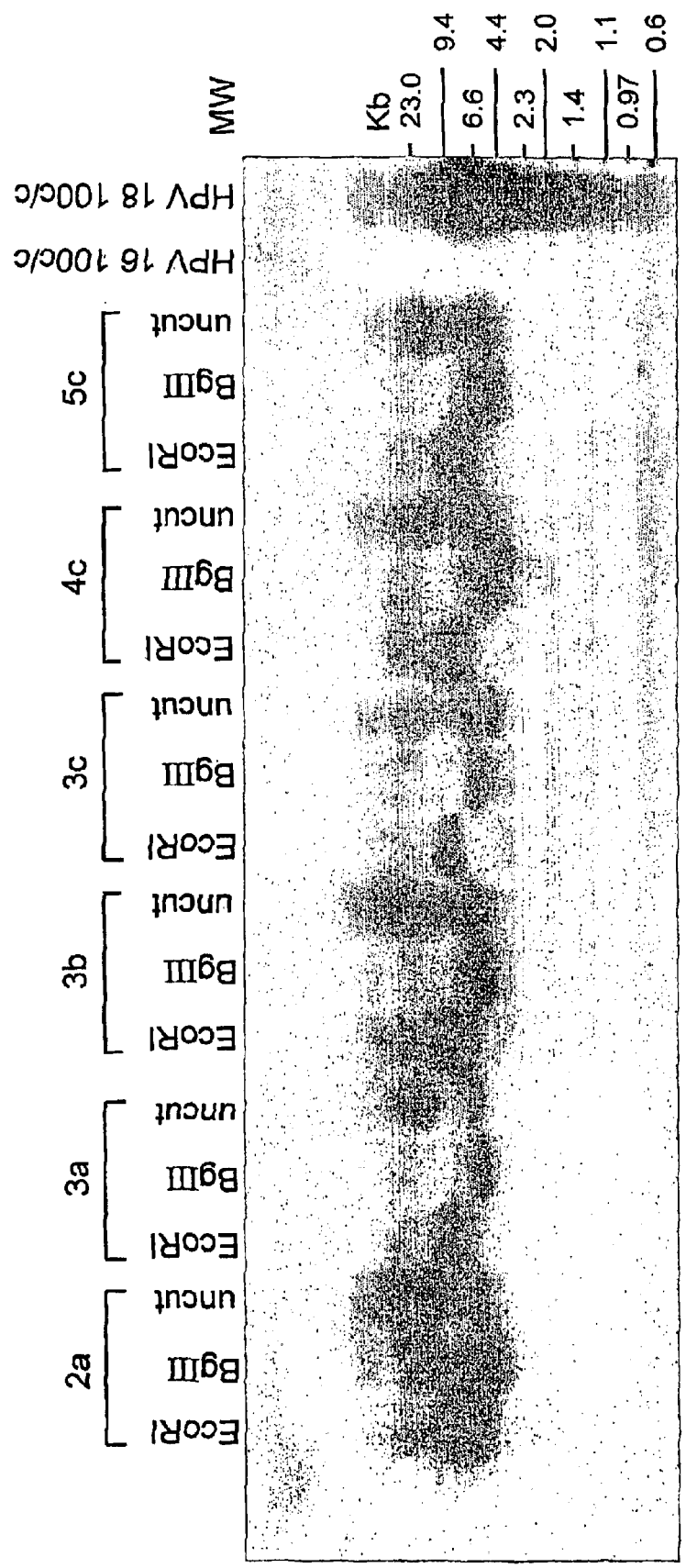
FIGS. 3A and 3B are Southern Blot analyses of clonal cell lines containing HPV. Several cell lines that had been transfected with HPV 18/16 chimeric DNA were evaluated for the presence of episomal viral DNA. DNA was isolated from each cell line, digested with either Eco RI restriction endonuclease, Bgl II restriction endonuclease or undigested, and evaluated by Southern blot. DNA probed with an HPV 18 specific probe (FIG. 3A) demonstrated that clones 2a, 3a, 3b, 3c, 4c, and 5c contained an approximately 8 kb band when digested with Eco RI, indicating that all viral sequences were episomal. A 5.6 Kb band was detected upon Bgl II digestion, further demonstrating that the episomal DNA contains the HPV 16 L2/L1 coding sequence. Undigested DNA show supercoiled and nicked genomic viral DNA. Southern blot analysis using an HPV 16 L2/L1 specific probe (FIG. 3B) confirmed the episomal nature of the viral DNA and verified the presence of the 2.4 Kb HPV 16 L2/L1 sequence within the chimeric viral DNA.
Figure 3B:
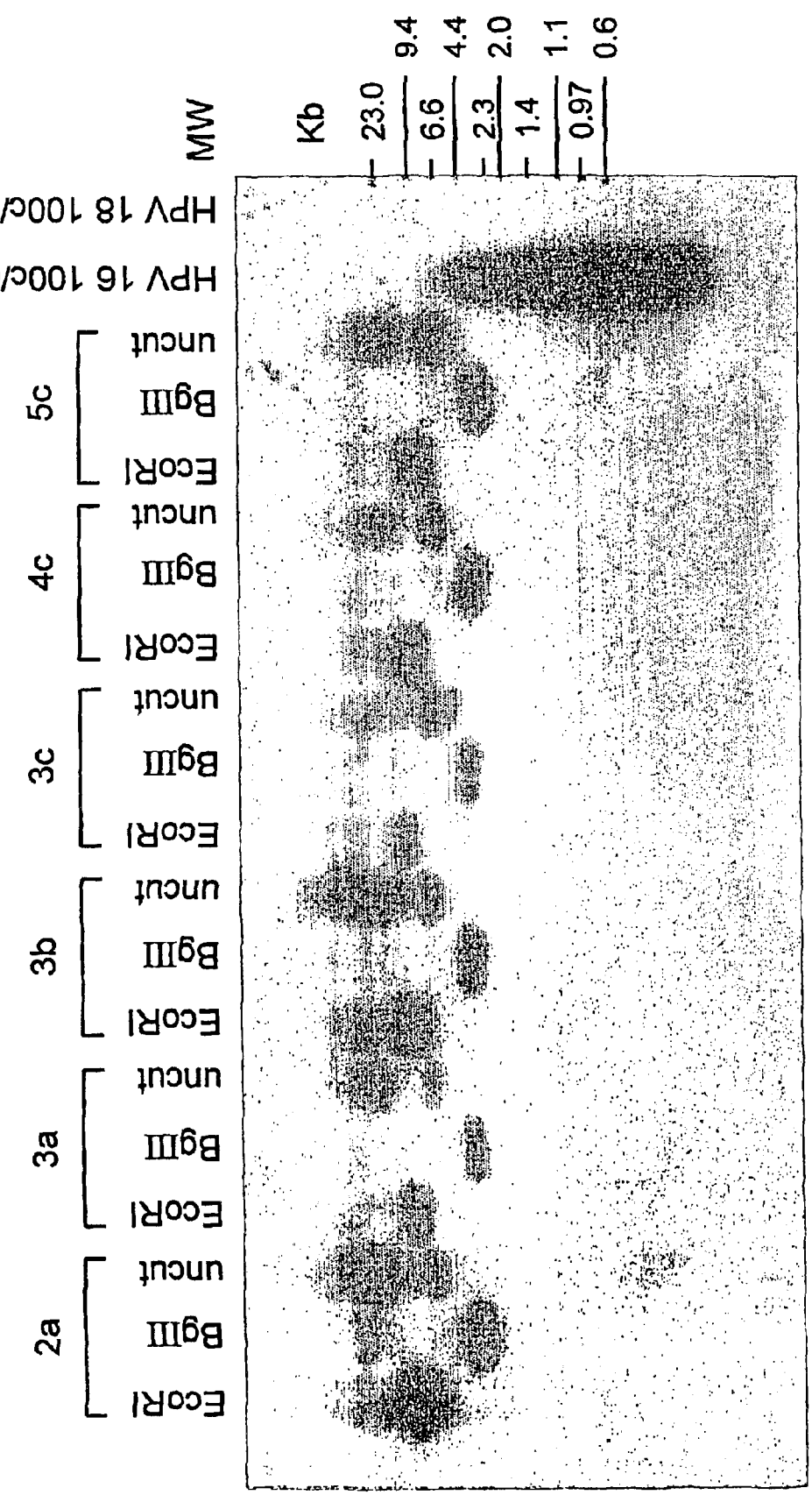
Figure 4:
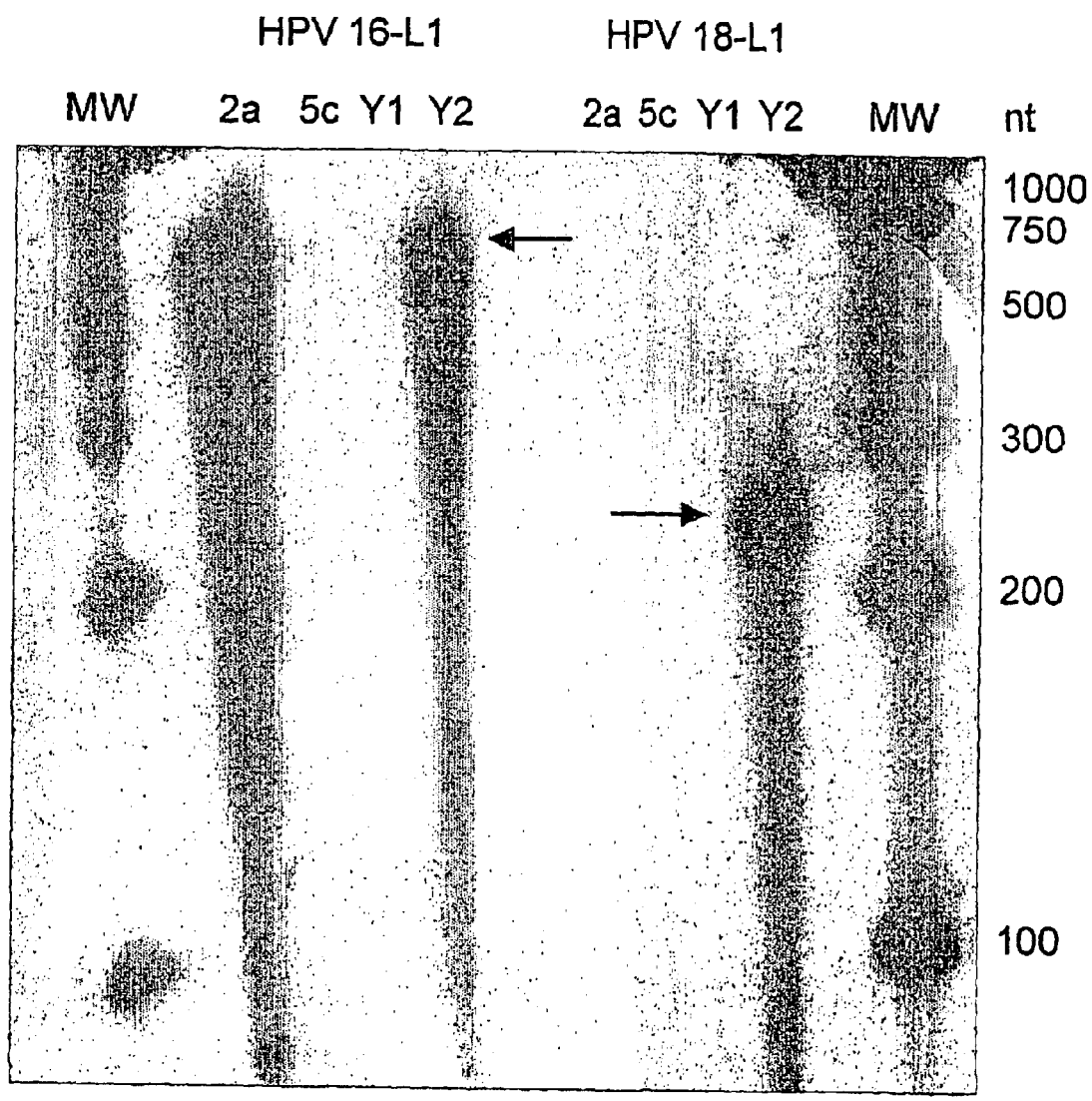
FIG. 4 is an RNA Protection Assay of clonal cell lines containing HPV. An RNA protection assay was performed on RNA extracted from cell lines 2a and 5c grown as raft cultures. Using an HPV 16 L1-specific riboprobe, clone 2c is shown to be generating a large amount of HPV 16 L1 specific RNA, while clone 5a is making a lesser amount. Y1 is a yeast derived RNA control digested with Rnases. Y2 is an undigested yeast RNA control.
Figure 5:
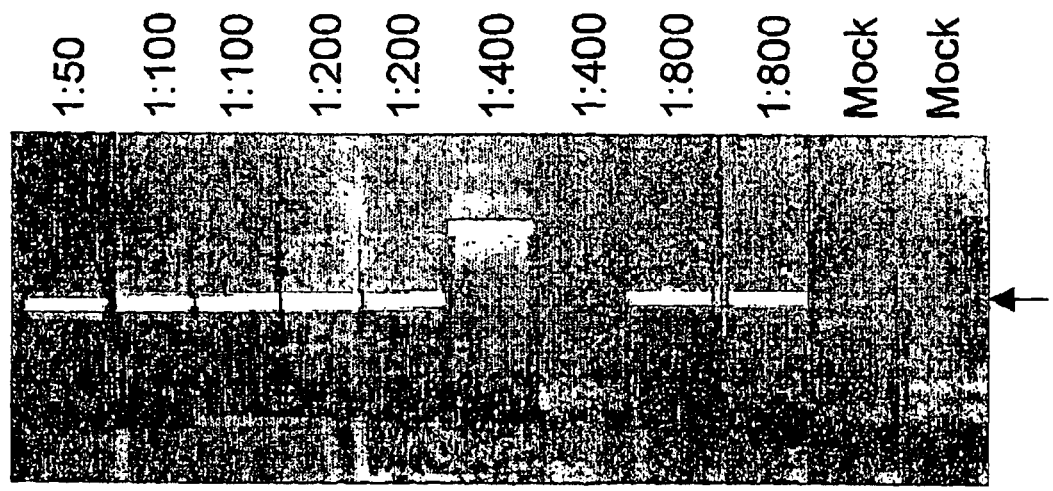

FIG. 5 is a demonstration of the presence of infectious chimeric virus. HaCat cells were infected with dilutions of virus from HPV18/16 chimeric clone 2A. Cells were harvested after 7 days and virus infection was detected by the presence of a 486 bp HPV 18 E1^E4 nested RT-PCT product (arrow). Virus dilutions are indicated above the figure. "Mock" indicates cells that were mock infected.

Figure 6A:
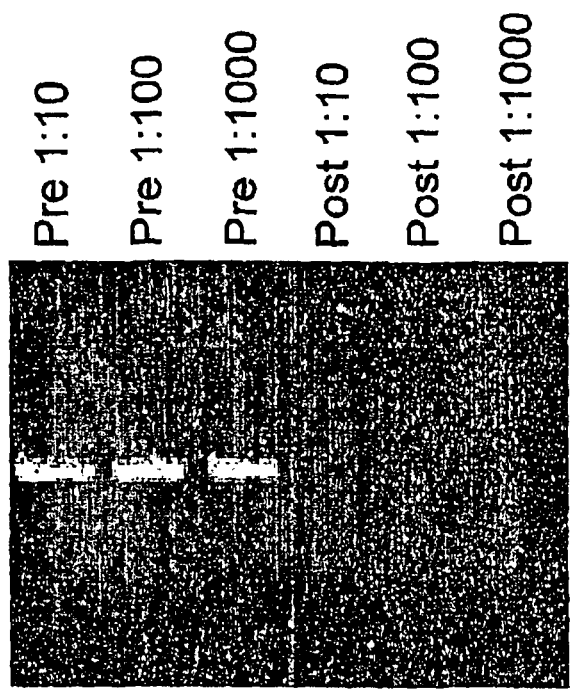
Figure 6B:
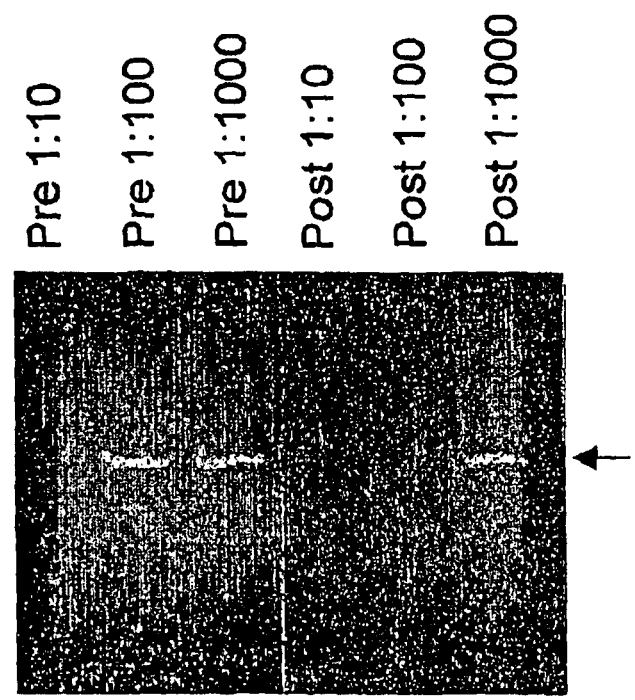

FIGS. 6A and 6B are demonstration of HPV 16 specific neutralization. HaCat cells were incubated in the presence of dilutions of Rhesus pre sera or post HPV 16 L1 VLP immunized sera and then chimeric virus clone 2A was added. Cells were harvested after 7 days and virus infection was detected by the presence of a 486 bp HPV 18 E1^E4 nested RT-PCR product (arrow). Serum dilutions are indicated above the figure. Figures A and B represent results from two different Rhesus monkeys.

As used throughout this specification and claims, the following terms apply:

Infectious—a virus is infectious if it can replicate in a suitable host cell. This is to distinguish the virus from a virus like particle (VLP) which is made up of an empty capsid protein(s) containing no nucleic acid, and thus cannot replicate in any cell.

HPV has been an especially difficult virus to grow in cell culture, since its early genes appear to be active only in undifferentiated cells, while its late genes (encoding structural proteins for capsid formation) are active in differentiated cells. However, it is known that infectious HPV 18 can be grown in raft cultures, as is described in U.S. Pat. No. 5,994,115, which is hereby incorporated by reference.

In accordance with this invention it has been found that the raft culture system used for HPV 18 will support growth of infectious chimeric papillomaviruses.

The chimeric viruses of this invention generally have two sources for their genome. The first source contributes to the viral early genes. Early genes encode for and expresses the non-structural proteins of papillomavirus that are required for the production of infectious virus. These genes include E1, E1^E4 (a spliced transcript, part of the RNA comes from E1 and the other from E4), E2, E3, E4, E5, E6, and E7.

A second source of DNA contributes the genes encoding the late genes, L1 and L2. These sequences allow for the production of the L1 and L2 structural proteins that assemble into infectious virus particles containing the chimeric viral genomic DNA.

In preferred embodiments of this invention the source of the early genes is a human papillomavirus, and particularly HPV 18. It should be recognized however, that other serotypes of viruses are also operable in this invention, and references to HPV18 as the source of early genes is meant to be illustrative, and not limiting.

The source of the late genes may be any papillomavirus, human or non-human. Particularly preferred sources include HPV 6a, 6b, 11, 16, 18, other disease-associated HPVs. Other serotypes include HPV 1, HPV 31, HPV 33, HPV 35, HPV 39, HPV 41, HPV 47, HPV 51, HPV 57, and HPV 58. Also preferred serotypes include animal papillomaviruses, especially those from papillomaviruses used in animal disease models, such as cottontail rabbit papillomavirus (CRPV), bovine papillomavirus (BPV) and canine oral papillomavirus (COPV). All that this needed is for the researcher to have the access to a L1 and or L2 gene sequence so that it can be cloned using techniques described herein. The sequences of numerous human and animal papillomavirus L genes are known.

Thus one aspect of this invention is an infectious chimeric papillomavirus. In preferred embodiments, the chimeric papillomavirus of this invention is selected from one of the following viruses (the first portion of the nomenclature refers to the source of the Early genes; the second portion of the nomenclature refers to the source of the Late genes): HPV18-16, HPV18-11, HPV18-6a, HPV18-6b, HPV 18-31, HPV 18-33, HPV 18-35, HPV 18-39, HPV 18-41, HPV 18-42, HPV 18-47, HPV 18-51, HPV 18-57, HPV 18-58, HPV 18-COPV, HPV18-BPV, HPV18-CRPV.

The chimeric virus genome can be assembled using plasmids and standard molecular biological techniques. Briefly, this is accomplished by generating a DNA fragment containing the coding sequence of the papillomavirus structural L1 and L2 genes and cloning this DNA into the appropriate location of a plasmid which contains the early genes of HPV 18 necessary for virus replication.

The chimeric viruses of this invention are grown in a raft culture system (also referred to as an organotypic culture system). Briefly, a dermal equivalent is made from a mixture of type I collagen and fibroblasts. Cells from a cell line derived from differentiating epithelia cells are placed on the top of the dermal equivalent, and while submerged, are allowed to grow to confluence. The dermal equivalent with epithelial cells on top is then lifted onto a wire grid where it remains at an air-liquid interface. From this point on the epithelial cells never come in contact with the culture media. Feeding of the epithelial cells is done by diffusion through the dermal equivalent. The epithelial cells will stratify and differentiate over approximately a two week period. Preferably, and inducer of protein kinase C is added to the media, and the cells which have maintained episomal copies of the chimeric viral DNA will biosynthesize virions.

One of the significant uses of the chimeric viruses of this invention is in assays, and in particular neutralization assays. While there are assays in the art which assess whether a serum contains neutralizing antibodies, these assays all employ either a non-infectious virus, or are in vivo. The assay of this invention, in contrast can be performed in vitro, which is much more convenient for the researcher, and can use infectious particles. Thus, the results are more likely to mimic what really happens during an infection than what occurs in vitro. Further, since essentially the same procedure can be used to any chimeric papillomavirus, a large number of serotypes can easily be assessed, while using an identical culture method.

Thus another aspect of this invention is an assay to determine if a neutralizing antibody specific for a an epitope found on papillomavirus capsid is present in a sample comprising:

(a) contacting the sample with an infectious chimeric papillomavirus; and (b) determining if the infectivity of the chimeric virus is modulated.

In preferred embodiments of this invention, the infectious chimeric papillomavirus has a first source of genes encoding the early genes, and a second source encoding the late genes. These late genes are preferably from HPV 6, 11, 16 or 18. In other embodiments, the sample is a serum sample from an individual who is belied to have been exposed to the same serotype HPV as was the source of the late genes. Thus for example, if one wanted to determine if an individual has neutralizing antibodies to HPV 16, the chimeric virus should have HPV16 late genes; one example would be an HPV18-16 chimera. This assay is also useful in distinguishing between serotypes which are genetically closely related, such as HPV 6 and 11, whose late proteins differ by only a few amino acids.

One can determine if the infectivity of the chimeric virus is modulated in a number of ways. A change in virus infectivity is a relative measurement—i.e. a standard virus preparation can be generated which all other types are compared. In preferred embodiments of the neutralization assay, for example, the "no serum" positive control is the standard by which all reduction in infectivity is measured.

Another assay which is part of this invention detects whether a chimeric virus has actually infected (i.e. entered) cells, or whether it has merely bound to the surface, but has not yet invaded the cell. In this assay, a RT-PCR (reverse transcriptase-PCR) analysis of RNA transcripts derived from the early genes may be used. When the chimeric virus replicates within a human cell, a splice variant of the E1^E4 gene is made which is 486 bp long, rather than several Kb (which is the length of the unspliced viral genome). Thus, detection of the splice variant can be used as an indication that infection has occurred. The E1^E4 splice variant may be any one (sequences of E1 and E4 are known in the art. Preferred sequences are: (Oligonucleotides used as primers in the PCR amplification are underlined).

In addition, reporter genes may be introduced into the genomic DNA to improve the ability to detect infection. These chimeric viruses would be useful in evaluation of vaccines designed to elicit immune responses to papillomavirus proteins. In addition, they would provide a tool to study the molecular aspects of viral replication, and might play an important role in development of therapeutic treatments associated with papillomavirus infections.

The following non-limiting examples are presented to better illustrate the invention.

EXAMPLE 1

Generation of an HPV 18 Δ L2/L1 Transfer Plasmid

20 μg of PBS-HPV 18 plasmid (from Dr. Craig Meyers, Hershey Medical Center, Hershey, Pa.) was digested AatII (Boehringer Mannheim Cat #775207). Digested DNA was purified with a Centrisep column (Princeton Separations Cat #CS-901) and then digested with Afl II (New England Biolabs Cat #520S). The resulting 6647 bp band was gel purified using a QIAEX gel extraction kit (QIAGEN Cat #20021).

Using the following oligonucleotides (Midland Co.) and pfu Turbo DNA polymerase (Strategene), two PCR fragments were generated:

1. A 720 bp PCR product containing HPV 18 genomic DNA from nucleotide 3542 at the AatII site to the start of the HPV 18 L2 sequence at nucleotide 4246. The 5' side of the PCR fragment contains an AatII restriction site while the 3' side contains a BglII restriction site. The oligonucleotides used to generate the PCR product were

```
530
CAACCGAGCACGACAGGAACGACTCCAACGACGCAGAGAAACACAAGTA        (SEQ.ID.NO. 13)

TA

ATATTAAGTATGCATGGACCTAAGGCAACATTGCAAGACATTGTATTGCA

TTTAGAGCCCCAAAATGAAATTCCGGTTGACCTTCTATGTCACGAGCAATT

AAGCGACTCAGAGGAAGAAAACGATGAAATAGATGGAGTTAATCATCAA

CATTTACCAGCCCGACGAGCCGAACCACAACGTCACACAATGTTGTGTAT

GTGTTGTAAGTGTGAAGCCAGAATTGAGCTAGTAGTAGAAAGCTCAGCAG

ACGACCTTCGAGCATTCCAGCAGCTGTTTCTGAACACCCTGTCCTTTGTGT

GTCCGTGGTGTGCATCCCAGCAGTAAGCAACAATGGCTGATCCAGAAG
929

E1^E4 RNA spliced between nucleotides 929 and 3434:
3434
TACCAGTGACGACACGGTATCCGCTACTCAGCTTGTTAAACAGCTACAGC    (SEQ.ID.NO. 14)

ACACCCCCTCACCGTATTCCAGCACCGTGTCCGTGGGCACCGCAAAGACC

TACGGCCAGACGTCGGCTGCTACACGACCTGGACACTGTGGACTCGCGGA

GAAGCAGCATTGTGGACCTG 3603.
```

18 Aat II:                                    (SEQ.ID.NO. 1)
5'CGG CCA GAC GTC GGC TGC TAC ACG 3'

18 Bgl II B:                                 (SEQ.ID.NO. 2)
5'GCT AGC AGA TCT ACT TTT ATT ACA AAA ATA
CAA AAA GC 3'.

2. A 593 bp PCR product containing HPV 18 genomic DNA from nucleotide 7137 at the stop site of HPV 18 L1 to the AflII restriction site at nucleotide 7730. The 5' side of the PCR fragment contains a BglII restriction site while the 3' side contains an Afl II restriction site. The oligonucleotides used to generate the PCR product were:

18 Afl II:                                   (SEQ.ID.NO. 3)
5'GTA TGC AAT TAG CTT AAG TAA AAA CAA AC 3'.

18 Bgl II F:                                 (SEQ.ID.NO. 4)
5'GCT AGC AGA TCT TAT GTG TGT GTG TAT ATA
TAT ATA CAT C 3'.

The Aat II/Bgl II and Afl II/Bgl II PCR products were purified using a QIAquick PCR purification kit (Qiagen Cat #28104). The Aat II/Bgl II PCR product was digested with Aat II. The Afl II/Bgl II PCR product was digested with Afl II. The digested PCR products were purified using a QIAquick PCR purification kit (Qiagen Cat #28104).

The Afl II/Aat II digested plasmid was ligated with the two digested Aat II/Bgl II and Afl II/Bgl II PCR products. The resulting ligation was digested with Bgl II, purified with Genieprep, and ligated.

DH5 alpha (BRL Cat #18258) was transformed and colonies were screened for the correct plasmid which has the HPV 18 L2/L1 sequence replaced by a Bgl II cloning site. This new 7932 bp plasmid is referred to as pBS-HPV 18 Δ L2/L1.

EXAMPLE 2

Generation of Plasmid pBS-HPV 18/16 Containing HPV 16 L2/L1 Coding Sequences

The oligonucleotides listed below (Midland Co.) and pfu Turbo DNA polymerase (Strategene), were used to generate a 2.9 Kb PCR product containing HPV 16 L2 and L1 open reading frames. The DNA used for the PCR template was derived from HPV 16 L1/L2 genomic DNA from CasKi cells that had been cloned into pUC18. Both the 5' and 3' sides of the PCR fragment contain a Bgl II restriction site. The oligonucleotides used to generate the PCR product were:

16 L2 Bgl II F:                              (SEQ.ID.NO. 5)
5'GCT AGC AGA TCT ATG CGA CAC AAA CGT
TCT GCA AAA CG 3'

16 L1 Bgl II B:                              (SEQ.ID.NO. 6)
5'GCT AGC AGA TCT TTA CAG CTT ACG TTT
TTT GCG TTT AGC AG 3'

The 2.9 Kb HPV 16 L2/L1 PCR product was gel purified using the QIAEX II purification kit (QIAGEN). The purified product was digested with Bgl II, heat inactivated, and purified using Genieprep (Ambion Cat #1950). pBS-HPV 18 Δ L2/L1 was digested with Bgl II, dephosporylated with shrimp alkaline phosphatase (Boehringer Mannheim Cat #1758250), and heat inactivated with phosphatase at 65° C. for 15 minutes.

The Bgl II digested 2.9 Kb PCR product representing HPV 16 L2 and L1 open reading frames was ligated with Bgl II digested pBS-HPV 18 Δ L2/L1, resulting in a 10857 bp plasmid containing all of the HPV 18 genomic sequence except for the L2/L1 coding sequence which was replaced by the HPV 16 L2/L1 coding sequence. This plasmid was designated pBS-HPV 18/16.

EXAMPLE 3

Generation of Plasmid pBS-HPV 18/16 Containing HPV 16 L2/L1 Coding Sequences and a Mutated Eco RI Site The protocol for generating an infectious virus in raft cultures requires the release of the HPV genomic DNA prior to transfection into J2 cells. The HPV 18 genomic sequence does not contain an Eco RI site and this restriction endonuclease is used to release genomic DNA from the plasmid. The chimeric DNA plasmid pBS-HPV 18/16 contains an Eco RI site within the HPV 16 L2/L1 coding sequence. Site directed mutagenesis was performed using the Quick Change Site Directed mutagenesis Kit (Strategene Cat #200518) according to the manufacturers instructions. The following oligos were used to alter the Eco RI site without changing the amino acid sequence:

(SEQ.ID.NO. 7)
5'-CAT ACA TAC ATT CTA TGA ACT CCA CTA TTT
TGG AG 3' and
                                             (SEQ.ID.NO. 8)
5'CTC CAA AAT AGT GGA GTT CAT AGA ATG TAT
GTA TG 3'

The resulting plasmid was designated pBS-HPV 18/16M.

EXAMPLE 4

Generation of Chimeric Virus
Keratinocyte Electroporation Protocol with Chimeric Viral DNA The raft culture method described in U.S. Pat. No. 5,994,115 (which is hereby incorporated by reference) was essentially used to culture the cells. Briefly, the procedure used was as follows:

Plates of mitomycin C treated 3T3 J2 cells (10 cm dishes) were set up the day before the electroporation. These cells were split 1:3 and fed with E medium +5% FCS, and incubated overnight. pBS-HPV 18/16M plasmid DNA was digested with Eco RI to linearize and release the genomic chimeric viral DNA. Viral DNA was extracted with phenol/chloroform extract and a chloroform extract, EtOH precipitated, and resuspended at 10 μg/10 λ in TE [pH 8] buffer (based on starting weight). Salmon sperm DNA was prepared (denatured and sonicated) at 10 mg/ml. 500 mM BES [pH 7.2] stock in distilled sterile water was prepared.

Transfection

Salmon sperm DNA was boiled for 5 minutes and immediately placed on ice. and 10 λ of digested plasmid DNA, and 4.25 λ of salmon sperm DNA was aliquoted into 1.5 ml Eppendorf tubes.

Trypsinize and count keratinocytes. Resuspend using the following equation and media formulation.

cells=ml of E+10% FCS+5 mM BES [pH 7.2]

20×10⁶ cells/ml

A 250 λ cell solution (approximately 5×10⁶ cells) was made with the DNA mixtures from above. It was incubated at room temperature for 10 minutes. Solutions were transferred to an electroporation cuvette (BIO-RAD Gene Pulser Cuvette; cat #165-2088). Electroporation took place at 210 v/960 μFd using a BIO-RAD Gene Pulser. Cells were then incubated at room temperature for 10 minutes.

Each electroporation sample was then layered onto 10 ml of E+10% FCS; then centrifuged at approximately 300 rpm for 10 minutes. Each sample was resuspend in 6 ml of E+10% FCS.

The mitomycin treated J2 cells were refed with E+10% FCS (approximately 8 ml), then placed onto plates of mitomycin C treated J2 cells.

The following day, plates were refed with 10 ml of E+10% FCS+EGF, and re-fed every 2 days for approximately 7 days using E+10% FCS+EGF. After this time, plates were fed every 2 days with E+5% FCS+EGF. Mitomycin C treated feeders were on the cultures.

EXAMPLE 5

Generation of Raft Cultures

Raft cultures were generated to maintain the viral DNA in an episomal state and to generate infectious virus stocks. J2 feeder cells were trypsinized, and the concentration of viable cells was determined by trypan blue staining. A total of 6.25×10⁵ cells/mL was used for each raft.

J2 cells were centrifuged for 6 min and resuspended to 6.25×10⁵ cells/mL in reconstitution buffer. Rat tail collagen (type I) was added to each tube, along with 3 μL 10N NaOH per ml collagen mix per tube. Tubes were mixed by inverting for 5 min. 2.5 mL was aliquotted to each well of a 6-well cluster plate, and plates were incubated at 37° C. for 12–16 hr.

2 mL E-medium was added to the well and incubated. Epithelial cells were seeded onto the raft at a concentration of approximately 0.5–1.0×10⁶ epithelial cells per raft. They were incubated at 37° C. for 4 hr to over night and the medium was replaced when needed.

Cells were allowed to reach confluence, then a wire grid was placed in a 100 mm petri dish. The collagen gel was lifted onto the wire grid, and E medium was added until the under-side of the grid is full of medium but the medium was not allowed come through the holes of the grid. Epithelial cells were allowed to stratify and differentiate at the air/liquid interface.

For analysis, rafts were harvested by fixing in 4% paraformaldehyde, and the raft was embedded in paraffin. 4 μM sections were cut for immunohistochemistry.

Total cellular DNA was isolated from infected cells for Southern blot analysis. RNA was isolated from infected cells for RNA protection assays Virions were purified from raft cultures by CsCl isopycnic gradients and used for EM analysis as well as infectivity and neutralization assays.

EXAMPLE 6

Infectivity and Neutralization Assays

HaCat cells were seeded in 12 well plates at a density of 10⁵ cells/well, with growth media (10% fetal calf sera (Gibco), DMEM with high glucose (Gibco), 1× penicillin and streptomycin). The next day, media was aspirated from the cells and 100 μL of virus stocks serially diluted in Optimem (Gibco) were placed on the cells and incubated for 1 hour in a 37° C. 5% $CO_2$ incubator. For the neutralization assay, test sera were added to the cells prior to the addition of virus. After virus adsorption, fresh media was added to the wells and the cells were incubated for an additional 7 days. Total RNA was then isolated from the cells with Trizol (Life Technologies) according to the manufacturers instructions. 2 μg of total RNA was used in a one step RT-PCR reaction (Titan One Tube RT-PCR System, Boehringer Mannheim). The oligonucleotides used in the RT-PCR were:

Forward primer; nt 530-552: 5' CAA CCG AGC ACG ACA GGA ACG AC 3' (SEQ.ID.NO. 9) and Reverse primer; nt 3603-3582: 5' CAG GTC CAC AAT GCT GCT TCT C 3' (SEQ.ID.NO. 10)

The RT step was conducted at 50° C. for 30 minutes. This was followed by a PCR reaction with the following conditions: 95° C., 5 minutes followed by 40 cycles of 95° C., 15 seconds; 55° C. for 30 seconds; 72° C. for 30 seconds, and a final extension of 72° C., 7 minutes. 2 μL was removed from the first RT-PCR reaction and used in a subsequent PCR reaction with nested oligonucleotide primers (oligonucleotides 5' TCC AAC GAC GCA GAG AAA CAC 3' (forward primer; nt 553-573) (SEQ.ID.NO. 11) and 5' GAG TCC ACA GTG TCC AGG TC 3' (reverse primer; nt 3578-3558) (SEQ.ID.NO. 12).

Conditions for the second PCR reaction were as follows: 96° C., 60 seconds followed by 30 cycles of 94° C., 15 seconds; 65° C. for 30 seconds; 72° C. for 30 seconds, and a final extension of 72° C., 7 minutes. The nested PCR products were visualized on a 1% agarose gel containing EtBr. The presence of a 486 bp PCR product demonstrates that HaCat cells were infected by virus which produced an HPV 18 specific E1^E4 spliced transcript.

EXAMPLE 7

Generation of Cell Lines Containing HPV 18/16 Chimeric DNA

Several cell lines that had been transfected with HPV 18/16 chimeric DNA were evaluated for the presence of episomal viral DNA. DNA was isolated from each cell line, digested with either Eco RI restriction endonuclease, Bgl II restriction endonuclease or undigested, and evaluated by Southern blot. Eco RI will linearize genomic viral DNA resulting in a 7.9 Kb band if the DNA is episomal while Bgl II will release the 2.4 Kb HPV 16 L2/L1 coding sequence from the chimeric genomic viral DNA. Southern blot analysis of the DNA probed with an HPV 18 specific probe demonstrated that clones 2a, 3a, 3b, 3c, 4c, and 5c contained an approximately 8 kb band when digested with Eco RI, indicating that all viral sequences were episomal. A 5.6 Kb band was detected upon Bgl II digestion, further demonstrating that the episomal DNA contains the HPV 16 L2/L1 coding sequence. Undigested DNA show supercoiled and nicked genomic viral DNA. Southern blot analysis using an HPV 16 L2/L1 specific probe confirmed the episomal nature of the viral DNA and verified the presence of the 2.4 Kb HPV 16 L2/L1 sequence within the chimeric viral DNA.

EXAMPLE 8

Demonstration of HPV 16 L1 Transcription

In order to determine if the HPV 16 L1 coding sequence was being transcribed, an RNA protection assay was performed on RNA extracted from cell lines 2a and 5c grown as raft cultures. Using an HPV 16 L1-specific riboprobe, clone 2c is shown to be generating a large amount of HPV 16 L1 specific RNA, while clone 5a is making a lesser amount. Y1 is a yeast derived RNA control digested with Rnases. Y2 is an undigested yeast RNA control. As expected, no RNA was detected when using an HPV 18 L1-specific probe.

EXAMPLE 9

Immunohistochemical Analysis of Clones

Raft cultures of four clones were analyzed by immunohistochemistry for the presence of HPV 16 L1 protein. Raft cultures of clones 2a and 3a show many more HPV 16 L1 positive cells than clones 5c and 5e. Interestingly, clones 2a and 3a also demonstrate a greater number of koilocytes and display a more abnormal phenotype than clones 5c and 5e. These results are consistent with the fact that 2a contained more viral genomic DNA and HPV 16 L1 RNA than clone 5c.

EXAMPLE 10

Infectivity of Chimeric HPV 18/16 Virus

In order to determine if infectious chimeric virus was generated by raft cultures containing episomal copies of chimeric HPV 16/18 genomic DNA, a human karyotinocyte cell line (HaCat) was infected with serial dilutions of purified virus from clones 2a and 5c. Detection of a 486 bp HPV 18 E1^E4 spliced transcript by nested RT-PCR amplification was used to demonstrate infection of HaCat cells in vitro. HPV 18/16 chimeric virus isolated from clone 2a was still detected at a dilution of 1:800 while virus derived from clone 5c was only detected at the 1:50 dilution. This is consistent with previous results demonstrating that clone 5c contained less viral genomic DNA, HPV 16 L1 RNA, and HPV 16 L1 protein than clone 2a. No virus was detected in RNA isolated from mock infected HaCat cells, demonstrating the specificity of this assay. These results demonstrate for the first time the ability to generate infectious chimeric HPV virus.

EXAMPLE 11

HPV 16-specific Virus Neutralization

We were interested to see if this infectious HPV 18/16 chimeric virus containing the HPV 16 L2 and L1 structural proteins could be neutralized by HPV 16-specific polyclonal sera. HaCat cells were incubated in the presence of dilutions of either Rhesus pre sera or post HPV 16 L1 VLP immunized sera and then either a 150 or 1:100 dilution of the chimeric virus stock was added. After a 1 hour incubation, media was added to the cells and the cells were cultured for an additional 7 days. Total RNA was isolated and analyzed by RT-PCR for the presence of a 486 bp HPV 18 E^E4 spliced transcript, indicating that virus infection had occurred. Post-immunization serum from two Rhesus were able to inhibit viral infection at dilutions of 1:10 and 1:100. One of the two sera neutralized virus at 1:1000. Similar dilutions of pre sera had no effect on infectivity, demonstrating that virus neutralization not due to non-specific serum effects. Neutralization with immune sera generated against HPV 18 VLPs also had no effect, further demonstrating the specificity of the results.

What is claimed is:

1. An infectious chimeric papillomavirus comprising early genes and late genes, wherein the early genes are from HPV18 and the late genes are from a second papillomavirus source.

2. An infectious chimeric papillomavirus according to claim 1 wherein the late genes are from a source selected from the group consisting of: HPV 6a, HPV 6b, HPV 11, HPV 16, HPV 18, HPV 31, HPV 33, HPV 35, HPV 39, HPV 41, HPV 42, HPV 47, HPV 51, HPV 57, HPV 58, bovine papillomavirus, cottontail rabbit papillomavirus, and canine papillomavirus.

3. A vector encoding the chimeric infectious papillomavirus of claim 1.

4. A host cell comprising the chimeric infectious papillomavirus of claim 1.

5. A method of obtaining an infectious chimeric papillomavirus comprising:
   (a) preparing a chimeric papillomavirus which comprises early genes and late genes, wherein the early genes are from HPV18 and the late genes are from a second papillomavirus source;
   (b) preparing a raft cell culture of differentiating epithelial cells;
   (c) infecting the cell culture with the chimeric papillomavirus;
   (d) incubating the cell culture under conditions which support viral replication; and
   (e) harvesting the resultant chimeric papillomavirus.

6. A method according to claim 5 wherein the late genes are from a source selected from the group consisting of: HP 6a, HPV 6b, HPV 11, HPV 16, HPV 18, bovine papilloma virus, cottontail rabbit papillomavirus, and canine papillomavirus.

7. An assay to detect the presence of a human papillomavirus neutralizing antibody in a serum comprising:
   (a) contacting a cell culture comprising an infectious chimeric papillomavirus with the serum, wherein the infectious chimeric papillomavirus comprises early genes and late genes, wherein the early genes are from HPV18 and late genes are from a second papillomavirus source; and
   (b) determining if chimeric papillomavirus replication occurs within the cell culture in the presence of the serum.

8. An assay according to claim 7 wherein step (b) comprises contacting nucleic acids from the chimeric virus with a reverse transcriptase, and amplifying the resultant cDNA.

9. An assay according to claim 8 further comprising comparing the amount of cDNA obtained to that from a control cell.

* * * * *